United States Patent
Nagano et al.

(10) Patent No.: US 6,417,392 B1
(45) Date of Patent: Jul. 9, 2002

(54) METHOD FOR PRODUCTION OF ALKYLAMINO(METH)ACRYLATE AND APPARATUS THEREFOR

(75) Inventors: Hideaki Nagano; Tadayoshi Kawashima; Tetsuya Kajihara, all of Himeji; Kaoru Iwasaki, Hyogo-ken; Sumio Nakashima, Himeji, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/164,796

(22) Filed: Oct. 1, 1998

(30) Foreign Application Priority Data

| Oct. 1, 1997 | (JP) | 9-268462 |
| Dec. 26, 1997 | (JP) | 9-359412 |
| Dec. 26, 1997 | (JP) | 9-359413 |

(51) Int. Cl.$^7$ .............................................. C07C 69/52
(52) U.S. Cl. ...................... 560/222; 560/217; 564/206; 523/310
(58) Field of Search ................. 523/310; 560/217, 560/222; 564/206

(56) References Cited

U.S. PATENT DOCUMENTS

| 2,138,763 A | * | 11/1938 | Graves | 526/260 |
| 3,872,161 A | * | 3/1975 | Fukuchi et al. | 560/217 |
| 4,187,120 A | * | 2/1980 | Kunin et al. | 127/46.2 |
| 5,476,883 A | * | 12/1995 | Abe et al. | 523/127 |

FOREIGN PATENT DOCUMENTS

| GB | 2162516 A | 2/1986 | ........... C07C/67/03 |
| JP | 54-163517 | 12/1979 | |
| JP | 3-112949 | 5/1991 | |
| JP | 4-95054 | 3/1992 | |
| JP | 5-85997 | 4/1993 | |
| JP | 6-256271 | 9/1994 | |
| JP | 6-271517 | 9/1994 | |

* cited by examiner

Primary Examiner—Paul J. Killos
Assistant Examiner—Taylor V. Oh
(74) Attorney, Agent, or Firm—Fish & Richardson P.C.

(57) ABSTRACT

In the operation of producing an alkylamino(meth)acrylate by the reaction of transesterification of an alkyl(meth) acrylate with an alkylamino alcohol, the alkyl alcohol by-produced during the transesterification is distilled in the form of an azeotropic mixture with the alkyl(meth)acrylate, the resultant distillate is purified with an ion-exchange resin and handled, on the other hand, the reaction solution is distilled to allow separation of the catalyst wherein is provided a method and apparatus for effecting, in the production of the alkylamino(meth)acrylate, the distillation under such a condition as represses the amount of in crease of the Michael adduct below 2%.

16 Claims, 3 Drawing Sheets

METHOD FOR PRODUCTION OF ALKYLAMINO(METH)ACRYLATE AND APPARATUS THEREFOR

BACKGROUND OF THE INVENTION

1. Field of the Invention

This invention relates to a method for the production of an alkylamino(meth)acrylate and an apparatus therefor. More particularly, it relates, in the production of an alkylamino (meth)acrylate by the reaction of transesterification of a corresponding alkyl(meth)acrylate with an alkylamino alcohol, to a method for the purification of an alkyl alcohol by-produced in the transesterification, a method for handling the purified alkyl alcohol, a method for the purification of the reaction solution resulting from the transesterification, and an apparatus for the method of purification.

2. Description of the Related Art

The production, by the reaction of transesterification of an alkyl(meth)acrylate represented by the formula (1):

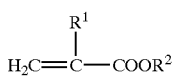
(1)

with an alkylamino alcohol represented by the formula (2):

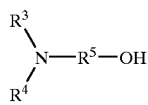
(2)

of an alkylamino(meth)acrylate represented by the formula (3):

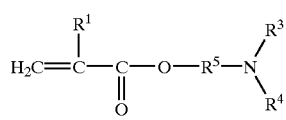
(3)

wherein the symbols are defined as described herein below, itself has been heretofore known from JP-A-4-95,054. This method consists in performing the reaction of transesterification while having the concentration of the alkylamino alcohol in the reaction system adjusted to not more than 25 mol %.

JP-A-5-85,997 describes, as a method for the production of a dialkylamino alkylacrylate, the reaction of transesterification which uses a dialkyl tin oxide as a catalyst and n-butyl acrylate as an alkyl acrylate and distills the reaction product under a reduced pressure to expel a by-produced n-butanol.

JP-A-3-112,949 discloses, concerning the recovery of a catalyst from the reaction solution obtained by the reaction of transesterification, a method which consists in distilling the reaction solution in the absence of oxygen.

JP-A-6-271,517 discloses a method for producing the alkylaminoalkyl ester of (meth)acrylic acid by the reaction of transesterification of a (meth)acrylic ester with an alkylamino alcohol.

JP-A-6-256,271 discloses a method for recovering by distillation a by-product which occurs during or remains after the production of the alkylamino alkyl ester of (meth) acrylic acid by the reaction of transesterification of a (meth) acrylic ester with an alkylamino alcohol.

JP-A-54-163,517 discloses a method which comprises a first step of performing a reaction of transesterification of the alkyl ester of (meth)acrylic acid with a dialkylamino alkanol, a second step of distilling the reaction mixture obtained by the first step thereby expelling the unaltered raw materials boiling at low temperatures, and a subsequent step of subjecting a mixture having a dialkylamino alkyl(meth) acrylate concentration of not less than 90% and obtained by the second step to distillation under a reduced pressure at a temperature in the range of 60–100° C.

SUMMARY OF THE INVENTION

Since the reaction of transesterification is an equilibrium reaction, it is caused to proceed simultaneously with the expulsion of the by-produced alkyl alcohol from the reaction system by distillation. In a commercial operation of this reaction, the expulsion is attained by providing a reaction vessel with a distillation column or tower (which will be referred to in the present invention as "alcohol distillation column") and allowing the by-produced alkyl alcohol to emanate in the form of an azeotropic mixture with an alkyl(meth)acrylate from the top of the column. Then, the distillate from the alcohol distillation column is further distilled, as occasion demands, to effect the recovery of the alkyl alcohol in the form of an azeotropic mixture with an alkyl(meth)acrylate via the top of the column and the recovery of the bottoms substantially comprising the alkyl (meth)acrylate via the bottom of the column, and the substances thus recovered are circulated to the reaction vessel and used again for the reaction of transesterification.

Since the alkyl alcohol recovered as described above (which will be occasionally referred to as "recovered alkyl alcohol") contains an alkyl(meth)acrylate, it is generally used as an alcohol moiety for the production of the alkyl (meth)acrylate by the reaction of esterification. When the plant for the production of the alkyl(meth)acrylate and the plant for the transesterification reaction are located at one site or at sites approximating closely to each other, these substances are stored severally in intermediate tanks when necessary and then conveyed by such means as pipes to the plant for the production of the alkyl(meth)acrylate. When the two plants are located at a great distance from each other, the substances may be stored as in storage tanks and transported by such means as tank lorries to the plant for the production of the alkyl(meth)acrylate.

When the recovered alkyl alcohol mentioned above is used as the alcohol moiety for the production of the alkyl (meth)acrylate, however, it has tended to induce degradation of the strongly acidic ion-exchange resin popularly used as a catalyst for esterification in the production of the alkyl (meth)acrylate and bring about such problems as impairing the yield of the alkyl(meth)acrylate aimed at and degrading the purity of the recovered alcohol after its storage for a certain duration.

An object of this invention, therefore, is to provide, for the operation of producing an alkylamino(meth)acrylate by the reaction of transesterification of an alkyl(meth)acrylate with an alkylamino alcohol, a method for recovering the alkyl alcohol by-produced during the reaction in a form ideal for use in the production of an alkyl(meth)acrylate, incapable of inducing degradation of purity during storage, and excellent in the stability of storage, a method for handling the recovered alkyl alcohol, and an apparatus therefor.

On the basis of the knowledge that, as taught in JP-A-4-95,054, the yield of the alkylamino(meth)acrylate aimed at is lowered during the reaction of esterification by the so-called Michael type addition reaction of the alkylamino alcohol as a raw material with the alkyl(meth)acrylate as a raw material or with the alkylamino(meth)acrylate produced, we have proposed a method for performing the reaction while keeping the concentration of the alkylamino alcohol in the reaction system adjusted to not more than 25 mol %. By this method, the reaction in process can be effectively prevented from entailing a secondary reaction.

It has been found, however, that since the alkyl(meth) acrylate, alkylamino alcohol, and alkylamino(meth)acrylate are distilled out of the reaction solution sequentially in the order mentioned even during the separation of the catalyst from the reaction solution by distillation, and, consequently, the alkylamino alcohol and the alkylamino(meth)acrylate are retained in a heated state during the interval between the termination of the distillation of the alkyl(meth)acrylate and the completion of the distillation of the alkylamino alcohol, such secondary reactions as the Michael addition of the alkylamino alcohol with the alkylamino(meth)acrylate tend to occur and, as a result, the yield of the alkylamino(meth) acrylate aimed at is lowered.

Another object of the invention, therefore, is to provide, for the operation of separating the catalyst from the reaction solution by distillation during the production of an alkylamino(meth)acrylate by the reaction of transesterification of an alkyl(meth)acrylate with an alkylamino alcohol, a method for producing the alkylamino(meth)acrylate in a high yield by effectively preventing secondary reactions and an apparatus therefor.

One aspect of the invention is directed to the provision of a method for producing an alkylamino(meth)acrylate by carrying out the reaction of transesterification of an alkyl (meth)acrylate with an alkylamino alcohol in the presence of a catalyst, characterized by causing the alkyl alcohol by-produced during the transesterification to be distilled in the form of an azeotropic mixture with the alkyl(meth) acrylate and purifying the resultant azeotropic mixture with an ion-exchange resin thereby recovering the alkyl alcohol.

Another aspect of the invention is directed to the provision of a method for the handling of the purified alkyl alcohol mentioned above, which consists in handling the purified alkyl alcohol at a temperature in the range of 0–50° C.

A further aspect of this invention is directed to the provision of an apparatus for the production of an alkylamino(meth)acrylate, characterized by comprising a transesterification reaction vessel (A) for carrying out the reaction of transesterification of an alkyl(meth)acrylate with an alkylamino alcohol in the presence of a catalyst while removing a by-produced alkyl alcohol from the top thereof as a distillate, an alcohol distillation column (B) for removing the by-produced alkyl alcohol, which emanates from the transesterification reaction vessel (A), in the form of an azeotropic mixture with the alkyl(meth)acrylate through the top thereof, and an ion-exchange resin purifying column (D) for purifying the mixture, which emanates from the alcohol distillation column (B), thereby recovering the alkyl alcohol.

In the present invention, the alkyl acrylate and the alkylmethacrylate will be referred to collectively as "alkyl(meth) acrylate."

Since the purified alkyl alcohol obtained by the method of production, method of handling, and apparatus therefor according to the invention has a decreased content of the basic nitrogen compound fated to poison the catalyst for the production of the alkyl(meth)acrylate, it can be satisfactorily utilized as an alcohol moiety for the production of the alkyl(meth)acrylate.

Further, since the purified alkyl alcohol obtained by the method of production, method of handling, and apparatus therefor according to the invention can prevent the alkyl alcohol and the alkyl(meth)acrylate contained therein from inducing a secondary reaction, it excels in stability of storage and enjoys stable storage for a long time at no sacrifice of purity.

By the method and apparatus according to the invention, the alkylamino(meth)acrylate can be produced with a high yield.

By the method and apparatus according to the invention, the formation of a viscous substance in the reaction solution can be repressed and the extraction of the catalyst from the distillation column can be attained easily.

DESCRIPTION OF THE PREFERRED EMBODIMENTS

Figure 1:
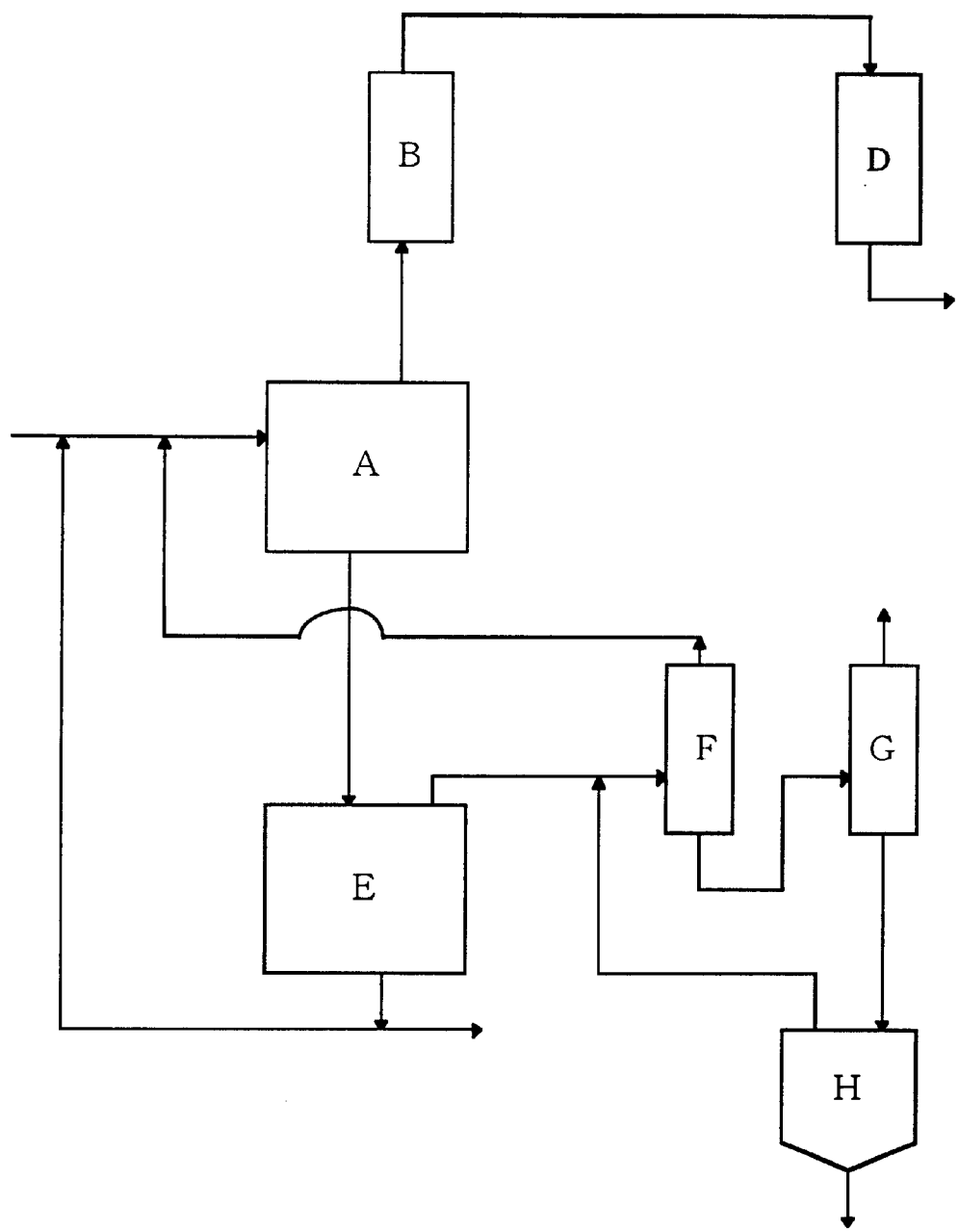
FIG. 1 is a process diagram representing one method for producing an alkylamino(meth)acrylate according to the invention.

We have pursued a diligent study concerning the reaction of transesterification using dimethylamino ethanol as an alkylamino alcohol and methyl acrylate as an alkyl(meth) acrylate and forming methanol as a by-produced alkyl alcohol to acquire the following pieces of knowledge.

(1) The reaction of transesterification induces such secondary reactions as form trimethylamine, methyl dimethylamino-propionate, and acetaldehyde.

(2) The trimethylamine, methyl dimethylamino propionate, and acetaldehyde distill out of the alcohol distillation column and mingle into the distillate. Even when the distillate is supplied to the next distillation column and further distilled therein, trimethylamine, acetaldehyde, and only a small amount of methyl dimethylamino propionate are distilled. The recovered methanol, therefore, inevitably incorporates therein trimethylamine, methyl dimethylamino propionate, and acetaldehyde. It is suspected that in these impurities, particularly trimethylamine and methyl dimethylamino propionate poison the catalyst for the production of the alkyl(meth)acrylate and deteriorates the efficiency thereof.

(3) It is suspected that when the recovered methanol has trimethylamine and methyl dimethylamino propionate incorporated therein, these impurities serve as a catalyst for inducing the Michael addition reaction and, consequently, give birth to methyl methoxypropionate and lower the purity of the recovered methanol.

As a means for eliminating the basic nitrogen oxide which poisons the catalyst for the production of the alkyl(meth) acrylate and, moreover, forms a cause for lowering the purity of the recovered alkyl alcohol, a method which consists in adding an acidic aqueous solution to the reaction solution thereby neutralizing and extracting the basic nitrogen oxide may be conceived. Since this method suffers the alkyl alcohol to migrate into the water phase and, consequently, requires the alkyl alcohol to be recovered again from the water phase as by distillation, it does not deserve to be called commercially advantageous on account of complexity of operation.

The present inventors, after further continuing the study, have discovered that the basic nitrogen oxide can be efficiently removed by purifying the recovered methanol of the quality mentioned above with an acidic ion-exchange resin, for example. This invention has been perfected as a result.

Our further diligent study has led to the acquisition of the following knowledge:

(4) The alkylamino(meth)acrylate aimed at can be produced with a high yield fully satisfactory from the commercial point of view by repressing the amount of the Michael adduct by-produced during the separation of the catalyst from the reaction solution, namely the ratio of increase of the Michael adduct which will be described specifically herein below, below a specific level, (5) When the catalyst is separated by distillation from the reaction solution formed by the reaction of transesterification, the ratio of increase of the Michael adduct can be lowered not by using one distillation column and sequentially distilling an alkyl(meth)acrylate, alkylamino alcohol, and alkylamino(meth)acrylate in the order mentioned as practiced conventionally but by using two distillation columns, distilling an alkyl(meth)acrylate from the reaction solution in the first distillation column, then distilling an alkylamino alcohol and alkylamino(meth) acrylate quickly from the remainder of the reaction solution in the second distillation column, and separating the catalyst via the bottom of the second distillation column, (6) Particularly by using a thin layer distillation column (thin layer type evaporator) as the second distillation column, the duration of heating in the thin layer distillation column can be curtailed and the increase of the Michael adduct can be effectively prevented and, as a result, the alkylamino(meth)acrylate aimed at can be obtained with a high yield, and (7) The formation of a viscous substance in the reaction solution is diminished and the extraction of the catalyst from the second distillation column is facilitated.

The invention has been perfected based on this knowledge.

The invention will be described below by reference to modes of embodiment thereof.

Though the alkyl(meth)acrylate to be used in the invention is not particularly limited, it is preferred to be an alkyl(meth)acrylate which is represented by the formula (1):

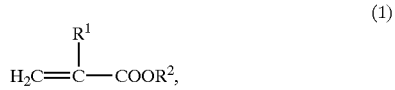

(1)

wherein $R^1$ denotes a hydrogen atom or a methyl group and $R^2$ denotes an alkyl group of 1–4 carbon atoms. As typical examples of the alkyl(meth)acrylate, methyl(meth)acrylate, ethyl(meth)acrylate, n-propyl(meth)acrylate, n-butyl(meth) acrylate, 2-ethylhexyl(meth)acrylate, and n-octyl(meth) acrylate may be cited. Among other specific alkyl(meth) acrylates cited above, methyl(meth)acrylate, ethyl(meth) acrylate, and n-butyl(meth)acrylate prove particularly advantageous.

Though the alkylamino alcohol to be used in this invention is not particularly limited, it is preferred to be an alkylamino alcohol which is represented by the formula (2):

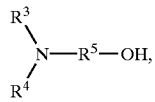

(2)

wherein $R^3$ denotes a hydrogen atom or an alkyl group of 1–8 carbon atoms, $R^4$ an alkyl group of 1–8 carbon atoms, and $R^5$ an alkylene group of 1–4 carbon atoms. As typical examples of the alkylamino alcohol, dimethylamino ethanol, diethylamino ethanol, dipropylamino ethanol, dibutylamino ethanol, dipentylamino ethanol, dihexylamino ethanol, dioctylamino ethanol, methylethylamino ethanol, methylpropylamino ethanol, methylbutylamino ethanol, methylhexylamino ethanol, ethylpropylamino ethanol, ethylbutylamino ethanol, ethylpentylamino ethanol, ethyloctylamino ethanol, propylbutylamino ethanol, dimethylamino propanol, diethylamino propanol, dipropylamino propanol, dibutylamino propanol, butylpentylamino propanol, and t-butylamino ethanol may be cited. Among other specific examples of the alkylamino alcohol mentioned above, dimethylamino ethanol and ethylamino ethanol prove particularly advantageous.

As typical examples of the alkylamino(meth)acrylate represented by the formula (3):

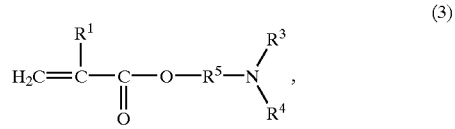

(3)

wherein the symbols have the same meanings as defined above, obtained by the reaction of transesterification of the alkyl(meth)acrylate of the formula (1) with the alkylamino alcohol of the formula (2), dimethylamino ethyl(meth) acrylate, diethylamino ethyl(meth)acrylate, dimethylamino propyl(meth)acrylate, dimethylamino butyl(meth)acrylate, and dibutylamino ethyl(meth)acrylate may be cited.

The method itself for producing the alkylamino(meth) acrylate of the formula (3) by the reaction of transesterification of the (meth)acrylate of the formula (1) with the alkylamino alcohol of the formula (2) is disclosed in JP-A-4-95,054 as described above. The invention does not have any feature in this reaction of transesterification itself. This reaction of transesterification can be carried out as by adjusting the concentration of the alkylamino alcohol in the reaction system to not more than 25 mol %, using a catalyst and a polymerization inhibitor which have been arbitrarily selected, and adopting a procedure and conditions which have been arbitrarily selected as described in JP-A-4-95,054.

Figure 2:
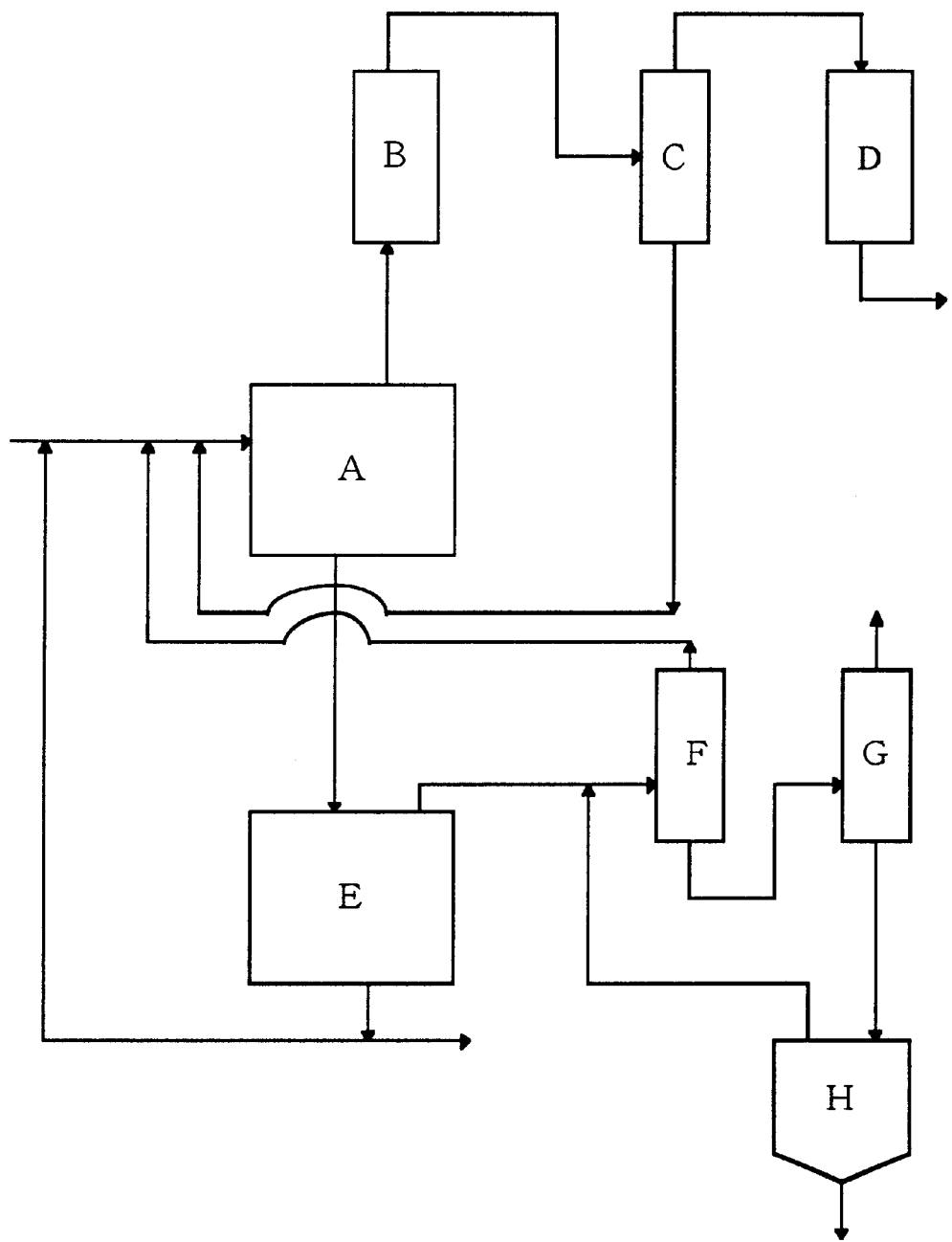
FIG. 2 is a process diagram representing another method for producing an alkylamino(meth)acrylate according to the invention.

Now, the invention will be described below with the aid of drawings. FIG. 1 is a process diagram illustrating one mode of embodying the method of the invention and FIG. 2 is a process diagram illustrating another mode of embodying the invention.

With reference to FIG. 1, first in the reaction vessel A, the reaction of transesterification of the alkyl(meth)acrylate of the formula (1) with the alkylamino alcohol of the formula (2) is carried out. Since the reaction of transesterification is an equilibrium reaction, the apparatus is provided with an alcohol distillation column B in observance of the established rule for separating and removing the by-produced alkyl alcohol thereby enabling the reaction to proceed and the by-produced alkyl alcohol is consequently distilled in the form of an azeotropic mixture with the alkyl(meth)acrylate.

The operating conditions for the alcohol distillation column B are not particularly limited. The distillation may be effected, for example, by using a multistage distillation column and operating this distillation column under conditions suitable for efficiently distilling the by-produced alkyl alcohol in the form of an azeotropic mixture with the alkyl(meth)acrylate such as normal pressure—reduced pressure, 40–120° C. of column top temperature, and 0.5–15 of reflux ratio.

The distillate containing the alkyl(meth)acrylate and the alkyl alcohol and emanating from the alcohol distillation column B is supplied to an ion-exchange resin purifying column D and purified therein. It generally suffices to allow the distillate to flow to an ion-exchange resin bed dowanwardly at normal room temperature under normal pressure.

Preferably, the distillate which contains the alkyl(meth) acrylate and the alkyl alcohol, which emanates from the alcohol distillation column B, is supplied to a distillation column C and distilled therein as illustrated in FIG. 2. Specifically, the distillate containing the alkyl(meth)acrylate and the alkyl alcohol, which emanates from the alcohol distillation column B, is supplied to the distillation column C and distilled therein so that the distillate containing the alkyl alcohol having an increased concentration and the alkyl(meth)acrylate may be extracted through the top of the column C and meanwhile the bottoms formed substantially of alkyl(meth)acrylate may be withdrawn through the bottom of the column C and circulated to the reaction vessel A and used again for the reaction of transesterification. By this distillation in the distillation column C, the alkyl(meth) acrylate content in the distillate containing the alkyl alcohol and the alkyl(meth)acrylate is lowered to the extent that the distillate can be suitably purified in the following purification step.

The operating conditions for the distillation column C are not particularly limited. The distillation may be attained, for example, by using a multistage distillation column and operating this distillation column under conditions suitable for recovering part of the alkyl(meth)acrylate in the form of bottoms. Though the conditions cannot be specifically defined because they vary with the composition of the distillate which contains the alkyl(meth)acrylate and the alkyl alcohol, the distillation is generally performed suitably under the conditions of normal pressure—reduced pressure, 40–120° C. of column top temperature, and 0.5–15 of reflux ratio.

The distillate containing the alkyl(meth)acrylate and the alkyl alcohol, which emanate from the distillation column C, is supplied to the ion-exchange resin purification column D and purified therein, similarly to the distillate containing the alkyl(meth)acrylate and the alkyl alcohol, which emanate from the alcohol distillation column B mentioned above.

The ion-exchange resin to be used in the purification column D may be an acidic ion-exchange resin. This acidic ion-exchange resin uses a phenol type resin, a styrene type resin, or a (meth)acrylic acid type resin for its basis and assumes a form selected from the group consisting of gel type, porous type, and macroporous type, and contains at least one species of ion-exchange group selected from the group consisting of sulfonic acid group, alkylsulfonic acid group, and carboxyl group. The weakly acidic ion-exchange resin containing a carboxyl group as an ion-exchange group proves particularly advantageous among other species of acidic ion-exchange resin mentioned above.

The preeminence of the weakly acidic ion-exchange resin is as follows. The strongly acidic ion-exchange resin containing a sulfonic acid group has the disadvantage of suffering this sulfonic acid group to fulfill the function of inducing a reaction between the acetaldehyde contained in the distillate in need of purification with an alkyl alcohol and, when the alkyl alcohol is methanol, for example, tend to form 1,1-dimethoxy ethane. Since the boiling point of 1,1-dimethoxy ethane is 64.5° C., a level approximating closely to the boiling point, 80° C., of methyl acrylate, the alcohol recovered after the purification, when used for the production of methyl acrylate, brings about the problem of circulating through and accumulating in the reaction system jointly with the methyl acrylate. In contrast, the weakly acidic ion-exchange resin containing a carboxyl group as an ion-exchange group is capable of efficiently removing the basic nitrogen compound mentioned above without inducing conversion of acetaldehyde to 1,1-dimethoxy ethane.

As concrete examples of the weakly acidic ion-exchange resin, Duolite C-433, C-464, C-470V, C-436, ES-460, and ES-462 (available from Rohm and Haas Company), Amberlite IRC-75, IRC-84, and IRC-50 (available from Rohm and Haas Company), Diaion WK-20, WK-10, and WK-11 (available from Mitsubishi Chemical Co., Ltd.in Japan), Lewatit CNP (available from Bayer AB), and Dowex CCR-2 (available from Dow Chemical Company) may be cited.

The degree with which the purification is carried out in the ion-exchange resin column D is properly such that the liquid containing an alkyl alcohol and an alkyl(meth)acrylate, which result from the purification, (hereinafter occasionally called "purified alkyl alcohol") has a total nitrogen content of not more than 0.002% by weight (20 ppm), preferably not more than 0.001% by weight (10 ppm). Incidentally, the term "total nitrogen content" as used herein refers to the total amount of nitrogen in the nitrogen-containing compound having as main components thereof trimethyl amine as the by-product mentioned above and methyl dimethylaminopropionate. The numerical values reported herein as the total amount of nitrogen have been determined by the following method.

Determination of Total Amount of Nitrogen

This determination is effected by the specified method using a total nitrogen microanalyzer (made by Mitsubishi Chemical Co., Ltd. in Japan and sold under the product code of "TN-05") and operating the analyzer under the conditions of non-aqueous sample, gas flow volumes of 600 ml of oxygen/min and 100 ml of argon/min, and temperatures of 800° C. at the inlet and 900° C. in the catalyst bed.

Preferably, the purification in the ion-exchange resin column D is carried out in the presence of water. The amount of water thus present in the column is properly in the range of 0.05–100% by weight, preferably 0.1–50% by weight, and more preferably 0.2–20% by weight, based on the weight of the distillate containing an alkyl alcohol and an alkyl(meth)acrylate, which enter the ion-exchange resin column D.

If the amount of water co-existing in the distillate is unduly small, the problem that the ion-exchange resin is colored and subsequently the purified alkyl alcohol is colored, will ensue. Conversely, if the amount of water co-existing is unduly large, the amount of the distillate to be purified will increase to the extent of increasing the cost of production and adversely affecting the storage and transportation.

The co-existence of the prescribed amount of water in the distillate may be achieved, for example, by introducing water into the conduit extending from the alcohol distillation column B or the distillation column C to the ion-exchange resin column D or by directly introducing water into the ion-exchange resin column D.

Though the conditions for handling the alkyl alcohol containing the alkyl(meth)acrylate or the purified alkyl alcohol are not particularly limited, the temperature is properly in the range of 0–50° C., preferably 5–40° C. The term "handling" as used herein means such acts as storing and transporting the purified alkyl alcohol.

The adjustment of the total nitrogen content in the alkyl alcohol containing the alkyl(meth)acrylate to a level of not more than 20 ppm may be achieved by some other methods.

One of the methods consists in mixing the alkyl alcohol containing the alkyl(meth)acrylate with water or an acidic aqueous solution and depriving the aqueous layer of a basic nitrogen compound by extraction. The amount of the water or the acidic aqueous solution to be used herein does not need to be particularly limited but may be suitably decided. As concrete examples of the acid which can be used for the preparation of the acidic aqueous solution, organic acids such as formic acid, acetic acid, propionic acid, acrylic acid, methacrylic acid, methoxypropionic acid, butoxypropionic acid, oxalic acid, maleic acid, succinic acid, malic acid, and citric acid and inorganic acids such as hydrochloric acid, phosphoric acid, phosphorous acid, sulfuric acid, paratoluenesulfonic acid, boric acid, and nitric acid may be cited. The acid concentration does not need to be particularly limited but may be suitably decided.

Since the purified alcohol obtained as described above has been sufficiently deprived of the basic nitrogen compound fated to poison the catalyst for the production of the alkyl (meth)acrylate and is now has a small content of the basic nitrogen compound, it can be properly used as an alcohol moiety in the production of an alkyl(meth)acrylate. Further, it can prevent the alkyl alcohol from reacting with the alkyl(meth)acrylate and allow effective prevention of the purified alcohol in the process of storage or transportation from degradation of purity.

The purified alcohol is stored in a tank, when necessary, and then transferred to a plant for the production of an alkyl(meth)acrylate, and used as an alcohol moiety for the production of an alkyl(meth)acrylate.

Now, the reaction solution extracted from the reaction vessel A is supplied to a catalyst recovering device E and heated therein to induce distillation through the top of the vessel nascent alkylamino(meth)acrylate, unaltered alkyl (meth)acrylate, and unaltered alkylamino alcohol and extraction and recovery through the bottom thereof of the catalyst. The catalyst thus recovered can be circulated to the reaction vessel A and put to use again. The catalyst has the performance thereof gradually degraded when it is repeatedly used in the reaction. Usually, it is no longer circulated but discarded after the degradation has advanced to a prescribed level.

In the expulsion of the alkylamino(meth)acrylate, alkyl (meth)acrylate, and alkylamino alcohol mentioned above by distillation, it is proper to effect first the distillation under the conditions of normal pressure to a reduced pressure of the order of 50 mmHg and a reactor internal temperature in the range of 50–140° C. to expel the first fraction mainly containing the alkyl(meth)acrylate and subsequently the distillation under the conditions of 100–5 mmHg and 60–140° C. to expel the fraction mainly containing the alkylamino(meth)acrylate. In this case, the first fraction containing the alkyl(meth)acrylate is circulated to the reaction vessel A and the subsequent fraction containing the alkylamino(meth)acrylate is stored, as occasion demands, in an intermediate tank and then supplied to a light boiling separation column F and distilled therein, with the result that the alkyl(meth)acrylate and alkylamino alcohol emanating as light boiling components through the top of the separation column F will be circulated to the reaction vessel A. The bottoms containing the alkylamino(meth)acrylate is meanwhile supplied to a rectifying column G.

The light boiling separation column F is intended to separate a light boiling substance from the distillate from the catalyst recovering column E. Generally a multistage distillation column is adopted therefor and operated to effect the distillation under the conditions of 20–500 mmHg of reduced pressure, 60–140° C. of column top temperature, and 0.5–30 of reflux ratio.

The bottoms mainly containing an alkylamino(meth) acrylate, which emanates from the light boiling separation column F, is supplied to the rectifying column G and subjected to rectification therein, with the result that the alkylamino(meth)acrylate will be obtained through the top of the column G as a product. The rectifying column G does not impose any particular restriction on its operation conditions. Generally, a multistage distillation column is adopted for the rectifying column G and operated to effect distillation under the conditions of 5–150 mmHg of reduced pressure, 30–100° C. of column top temperature, and 0.3–10 of reflux ratio.

Since the bottoms of the rectifying column G still entrains a residue of alkylamino(meth)acrylate, it is proper for the bottoms to be supplied to a thin layer distillation column H and distilled therein, with the result that the distillate containing the alkylamino(meth)acrylate will be recovered and circulated to the light boiling separation column F. The bottoms emanating from the thin layer distillation column H is discarded as a waste.

The distillation in the thin layer distillation column H may be properly performed by using such a thin layer distillation device and such distillation conditions as are suitable for the distillation of alkylamino(meth)acrylate mentioned above. A vertical thin layer distillation device may be adopted and operated to effect distillation under the conditions of a reduced pressure and a temperature in the range of 60–140° C.

Now, this invention will be described below by reference to another embodiment.

The method itself for producing an alkylamino(meth) acrylate of the formula (3) by the reaction of transesterification of a (meth)acrylate of the formula (1) with an alkylamino alcohol of the formula (2) is disclosed in JP-A-4-95,054. JP-A-4-95,054 is incorporated herein by reference in its entirety. The present invention has no feature in the reaction of transesterification itself. This reaction of transesterification can be carried out as by adjusting the concentration of the alkylamino alcohol in the reaction system to not more than 25 mol %, using a catalyst and a polymerization inhibitor which have been arbitrarily selected, and adopting a procedure and conditions which have been arbitrarily selected as described in JP-A-4-95,054.

The present invention effects the removal of the catalyst by distillation from the reaction solution obtained by the reaction of transesterification under conditions such that the ratio of increase of the Michael adduct may be preferably not more than 2%, more preferably not more than 1.5%, and more especially not more than 1%. Use of two distillation columns for the separation of the catalyst by distillation from the reaction solution allows a further decrease of the ratio of increase of the Michael adduct to the neighborhood of 0.5%.

The term "Michael adduct" as used in this invention means the compounds represented by the following formulas (4), (5), (6), and (7) which are formed by the Michael addition of an alkyl(meth)acrylate of the formula (1) to an alkylamino alcohol of the formula (2), an alkyl(meth)acrylate of the formula (1) to a by-produced alkyl alcohol, an alkylamino(meth)acrylate of the formula (3) to an alkylamino alcohol of the formula (2), and an alkylamino(meth)acrylate of the formula (3) to a by-produced alkyl alcohol:

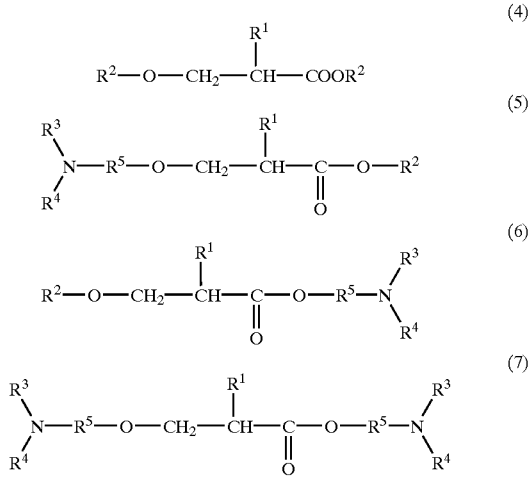

In the formulas (4)–(7) mentioned above, $R^1$–$R^5$ have the same meanings as defined in the formula (1)–(3) mentioned above.

The ratio of increase of the Michael adduct in this invention is determined by the following formula.

Ratio of increase of Michael adduct $(\%)=100\times(M)/(N)$ wherein (M)=(Weight of Michael adduct in distillate)+(Weight of Michael adduct in liquid of recovered catalyst)−(Weight of Michael adduct in reaction solution), (N)=(weight of reaction solution).

Here, the term "weight of Michael adduct in distillate" means the weight of the Michael adduct in the distillate obtained by the distillation of the reaction solution and, when two distillation columns are used, for example, means the total weight of the Michael adducts in the distillates obtained from the two distillation columns. The term "weight of Michael adduct in the liquid of recovered catalyst" means the weight of the Michael adduct in the catalyst (liquid) separated through the bottom of the distillation column. The weights of the Michael adduct which are reported herein have been determined by gas chromatography.

The method for properly adjusting the ratio of increase of the Michael adduct in the separation of the catalyst from the reaction solution by means of distillation, which has been obtained by the reaction of transesterification, consists in installing two distillation columns, first supplying the reaction solution to the first distillation column wherein it distills an alkyl(meth)acrylate through the top thereof, and then supplying the bottoms from the first distillation column to the second distillation column wherein it distills an alkylamino(meth)acrylate through the top thereof and separating the catalyst through the bottom thereof.

The distillation in the first distillation column mentioned above may be carried out under the conditions of 60–110° C. of column bottom temperature and two seconds–two hours of retention time, preferably 80–100° C. of column bottom temperature and five seconds–one hour of retention time.

The distillation in the second distillation column mentioned above may be carried out under the conditions of 60–120° C. of column bottom temperature and two seconds–one hour of retention time, preferably 80–110° C. of column bottom temperature and five seconds–30 minutes of retention time. Particularly, it is preferable to use a thin layer distillation column (thin layer distillation device) as the second distillation column mentioned above because this device is capable of curtailing the retention time and permitting effective repression of the increase of the Michael adduct.

A preferred embodiment of the invention resides in using a multistage distillation column as the first distillation column wherein it operates or effects distillation under the conditions of 60–110° C. of column bottom temperature and two seconds–two hours of retention time, and using a thin layer distillation column as the second distillation column wherein it operates or effects distillation under the conditions of 60–120° C. of column bottom temperature and two seconds–one hour of retention time.

Figure 3:
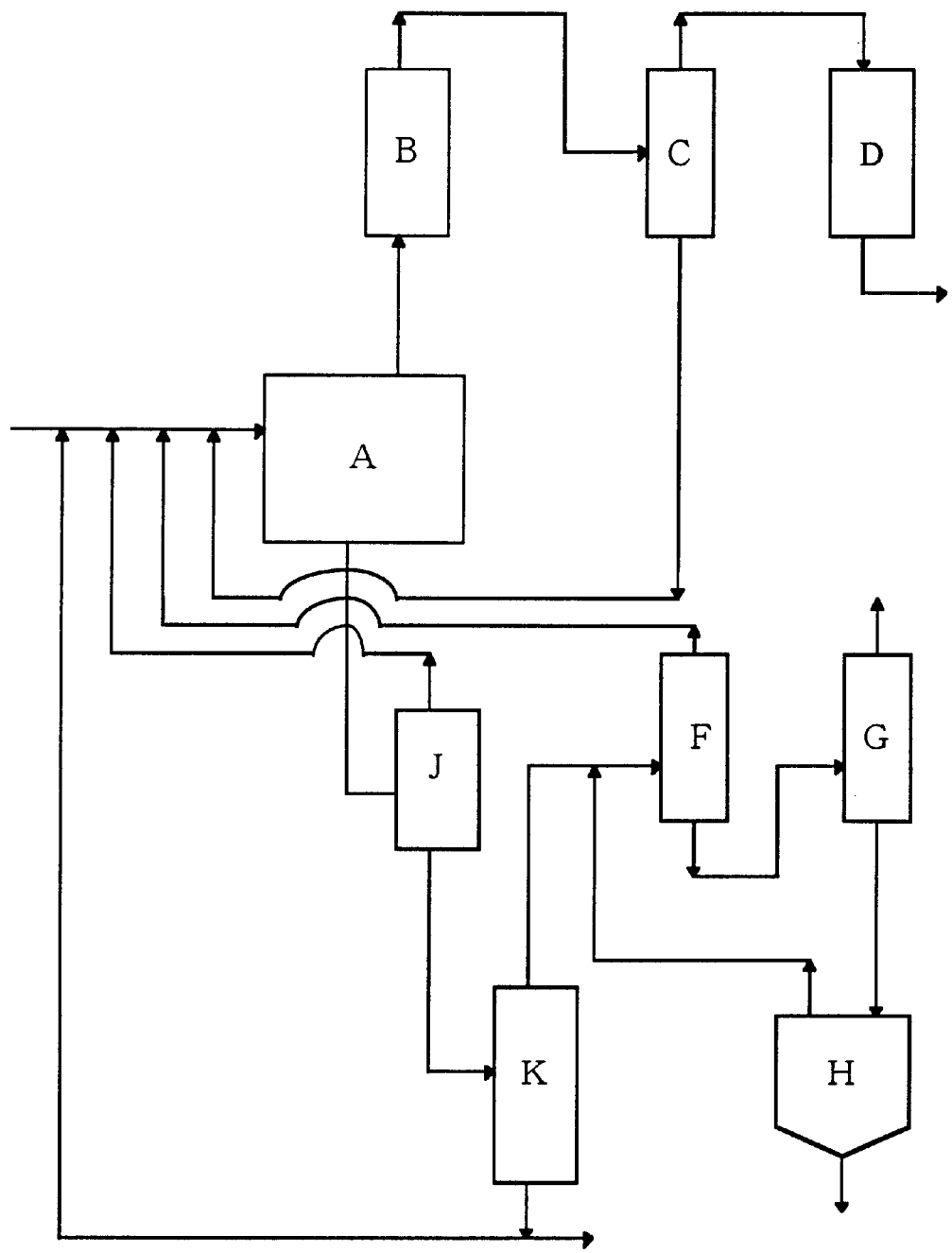
FIG. 3 is a process diagram representing still another method for producing an alkylamino(meth)acrylate according to the invention.

FIG. 3 is a process diagram illustrating one embodiment of the invention. Now, the method of the invention will be described below by reference to FIG. 3.

For a start, the reaction of transesterification of an alkyl (meth)acrylate of the formula (1) with an alkylamino alcohol of the formula (2) is carried out in the reaction vessel A. Since the reaction of transesterification is an equilibrium reaction, the apparatus in use is provided with an alcohol distillation column B in observance of the established rule for separating and removing the by-produced alkyl alcohol thereby enabling the reaction to proceed and the by-produced alkyl alcohol is consequently distilled in the form of an azeotropic mixture with the alkyl(meth)acrylate.

The alcohol distillation column B imposes no particular restriction on factors such as operating conditions. A multistage distillation column may be used wherein it is operated under suitable conditions such as normal pressure–reduced pressure, 40–120° C. of column top temperature, and 0.5–15 of reflux ratio which are ideal for efficient distillation of the by-produced alkyl alcohol in the form of an azeotropic mixture with an alkyl(meth)acrylate.

The reaction solution extracted from the reaction vessel A is stirred in an intermediate tank, as occasion demands, and then supplied to a distillation column J (equivalent to the first distillation column described above) and distilled therein, with the result that the alkyl(meth)acrylate will be distilled through the top thereof and circulated to the reaction vessel A. Properly, the distillation column J may be operated under the conditions of 60–110° C. of column bottom temperature, normal pressure–50 mmHg of column top pressure, and two seconds–two hours of column bottom retention time, preferably 80–100° C. of column bottom temperature, normal pressure–50 mmHg of column top pressure, and five seconds–one hour of retention time.

The bottoms of the distillation column J is supplied to a catalyst recovery column K (equivalent to the second distillation column described above) and distilled therein, with the result that an alkylamino(meth)acrylate and other compounds will be distilled through the top thereof and the catalyst will be separated and recovered through the bottom thereof. The catalyst thus recovered is generally circulated to the reaction vessel A. When the catalyst has lost activity to a prescribed level, it is discarded as a waste. Incidentally, since the catalyst is heated only for a short time, the formation of a viscous substance in the reaction solution is allayed and the extraction of the catalyst from the catalyst recovery column K is facilitated.

Properly, the catalyst recovery column K may be operated under the conditions of 60–120° C. of column bottom temperature, 200–5 mmHg of column top pressure, and two seconds–one hour of column bottom retention time, preferably 80–110° C. of column bottom temperature, 200–5 mmHg of column top pressure, and five seconds–30 minutes of column bottom retention time. Particularly, when a thin layer distillation column is used as the catalyst recovery column K, the retention time can be curtailed to a level in the range of 2–40 seconds at a column bottom temperature of 80–110° C.

The distillate containing the alkylamino(meth)acrylate and other substances which are distilled from the catalyst recovery column K, is supplied to a light boiling separation column F, with the result that light boiling substances are distilled through the column top and circulated to the reaction vessel A.

The light boiling separation column F imposes no particular restriction on factors such as design of device and operation conditions. It only requires to operate under conditions suitable for the separation of the light boiling substances from the distillate emanating from the catalyst recovery column K. Generally, a multistage distillation column maybe used as the light boiling separation column F wherein it is operated under the conditions of 20–500 mmHg of reduced pressure, 60–140° C. of column top temperature, and 0.5–30 of reflux ratio.

The bottoms mainly containing an alkylamino(meth)acrylate which emanate from the light boiling separation column F, is supplied to a rectifying column G and subjected to rectification therein, with the result that the alkylamino(meth)acrylate as a product will be obtained through the top thereof. The rectifying column G imposes no particular restriction on factors such as operating conditions. Generally, a multistage distillation column may be used as the rectifying column G wherein it is operated to effect distillation under the conditions of 5–250 mmHg of reduced pressure, 30–100° C. of column top temperature, and 0.3–10 of reflux ratio.

When the bottoms of the rectifying column G still entrains a residue of alkylamino(meth)acrylate, it is proper for the bottoms to be supplied to a thin layer distillation column H and distilled therein, with the result that the distillate containing the alkylamino(meth)acrylate will be recovered and circulated to the light boiling separation column F. The bottoms emanating from the thin layer distillation column H is discarded as a waste.

Concerning the distillation in the thin layer distillation column H, it suffices to use a thin layer distillation column wherein it operates under such conditions as are suitable for the distillation of the alkylamino(meth)acrylate mentioned above. For example, a vertical thin layer distillation column may be used and operated to effect distillation under a reduced pressure at a temperature in the range of 60–140° C.

For the purpose of recovering the by-produced alkyl alcohol obtained from the alcohol distillation column B and adapting it for use as an alcohol moiety for the production of an alkyl(meth)acrylate by the reaction of esterification, it is proper for the distillate containing the alkyl alcohol and the alkyl(meth)acrylate to be supplied to the ion-exchange resin column and purified therein. Since the step of purification is identical with that in the embodiment described above, a further description of the step or steps will be omitted.

EXAMPLES

Now, the invention will be described more specifically below with reference to examples. Wherever "parts" is mentioned, it means "parts by weight."

The expression <step for purification and recovery of alcohol> in the examples means a step of the invention which embraces the operation of a distillation column C and an ion-exchange resin column D, and the expression <step for purification of dimethylaminoethyl acrylate> therein means a step of the invention which embraces the operation of a catalyst recovery device E, a light boiling separation column F, a rectifying column G, and a thin layer distillation column H.

The contents of various components other than the total nitrogen contents reported herein below have been determined by means of gas chromatography.

Example I-1

A flask (reaction vessel A) having an inner volume of 3 liters and provided with a stirrer, a thermometer, and a fractional distillation column (alcohol distillation column B) was charged with 160.5 parts of dimethylamino ethanol, 1704.6 parts of methyl acrylate, 16.0 parts of dibutyl tin oxide as a catalyst, and 8.5 parts of phenothiazine as a polymerization inhibitor. The components in the flask were stirred and heated simultaneously. After they began refluxing, 641.8 parts of dimethylamino ethanol was added thereto so as to prevent the dimethylamino ethanol concentration in the reaction system from exceeding 10 mol %. This addition was made over a period of four hours. The methanol by-produced in the reaction under the conditions of 62–70° C. of column top temperature and 0.5–5.0 of ref lux ratio was distilled in the form of an azeotropic mixture with methyl acrylate. The reaction completed in eight hours. When the reaction solution was analyzed, the conversion of dimethylamino ethanol was found to be 95 mol % and the selectivity to dimethylaminoethyl acrylate to be 98 mol %.

<Step for Purification and Recovery of Alcohol>

The distillate containing methanol and methyl acrylate and emanating from the fractional distillation column (alcohol distillation column B) was placed in a distillation device (distillation column C) and subjected to distillation under the conditions of normal pressure, 62° C. of column top temperature, and 1.5 of ref lux ratio, with the result that an azeotropic mixture of methanol with methyl acrylate was extracted through the upper part and methyl acrylate through the lower part. The distillate from the upper part had the following composition.

Composition of Distillate from Distillation Device (Distillation Column C)

Methanol: 48.5 wt. %

Methyl acrylate: 51.3 wt. %

Acetaldehyde: 890 ppm 1,1-Dimethoxyethane: 70 ppm

Methyl methoxypropionate: 0.1 wt. %

Total nitrogen content: 93 ppm

The distillate emanating from the distillation device (distillation column C), after adding water at a ratio of 0.2 wt. %, was passed at normal temperature under normal pressure through a column packed with 200 ml of a weakly acidic ion-exchange resin (made by Mitsubishi Chemical Co., Ltd. and sold under the trademark designation of "Diaion WK-40") (ion-exchange resin column D). The liquid emanating from this column packed with the ion-exchange resin (ion-exchange resin column D) (purified alcohol) had the following composition.

Composition of Purified Alcohol (Initial Fraction)

Methanol: 48.5 wt. %

Methyl acrylate: 51.3 wt. %

Acetaldehyde: 890 ppm 1,1-Dimethoxyethane: 70 ppm

Methyl methoxypropionate: 0.1 wt. %

Total nitrogen content: 3 ppm

Even after 200 hours of starting the feed of raw materials, the ion-exchange resin was not colored and the purified alcohol was colorless and transparent.

When the purified alcohol was preserved at 30° C. for 10 days and then analyzed, it had the following composition, showing no change.

Composition of Purified Alcohol (After 10 Days of Preservation)

Methanol: 48.5 wt. %

Methyl acrylate: 51.3 wt. %

Acetaldehyde: 890 ppm 1,1-Dimethoxyethane: 70 ppm

Methyl methoxypropionate: 0.1 wt. %

Total nitrogen content: 3 ppm

Comparative Example I-1

When the distillate from the distillation device (distillation column C) obtained in Example I-1 was preserved at 30° C. for 10 days and then analyzed, it had the following composition. The composition of the distillate before the preservation is also shown.

Composition of Distillate

Methanol: 48.5 wt. %

Methyl acrylate: 51.3 wt. %

Acetaldehyde: 890 ppm 1,1-Dimethoxyethane: 70 ppm

Methyl methoxypropionate: 0.1 wt. %

Total nitrogen content: 93 ppm

Composition of Distillate after 10 Days of Preservation

Methanol: 48.0 wt. %

Methyl acrylate: 50.1 wt. %

Acetaldehyde: 890 ppm 1,1-Dimethoxyethane: 70 ppm

Methyl methoxypropionate: 1.8 wt. %

Total nitrogen content: 93 ppm

It is noted from the result given above that when the total nitrogen content was 93 ppm, the preservation lowered the concentrations of methanol and methyl acrylate and by-produced methyl methoxypropionate as an impurity.

Example I-2

The reaction of transesterification was performed by faithfully following the procedure of Example I-1.

<Step for Purification and Recovery of Alcohol>

Same as in Example I-1.

<Step for Purification of Dimethylaminoethyl Acrylate>

The reaction solution from the flask (reaction vessel A) was placed in a flask having an inner volume of 3 liters and provided with a stirrer, a thermometer, and a fractional distillation column (catalyst recovery column E) and treated therein under the conditions of normal pressure–100 mmHg and 75–90° C. of inner temperature to distill a fraction mainly containing methyl acrylate. Then, the distillation was continued under the conditions of 100–20 mmHg of pressure and 80–110° C. of inner temperature to obtain a distillate containing 73 wt. % of dimethylaminoethyl acrylate. A catalyst solution containing dibutyl tin oxide and phenothiazine was obtained through the bottom. This catalyst solution was utilized in the next round of reaction.

The aforementioned liquid containing 73 wt. % of dimethylaminoethyl acrylate was introduced into a fractional distillation device (light boiling separation column F) and subjected to distillation therein under the condition of 40 mmHg of column top pressure. Under the conditions of 50° C. of column top temperature and 5–20 of reflux ratio, methyl acrylate and dimethylamino-ethanol were fractionally distilled. A liquid containing 93 wt. % of dimethylaminoethyl acrylate was obtained through the bottom of the column.

The aforementioned liquid containing 93 wt. % of dimethylaminoethyl acrylate was introduced into a fractional distillation device (rectifying column G) and subjected to distillation therein under the condition of 25 mmHg of column top pressure. At a column top temperature of 76–79° C., dimethylaminoethyl acrylate was distilled. A liquid containing 70 wt. % of dimethylaminoethyl acrylate was obtained through the bottom of the column.

The aforementioned liquid containing 70 wt. % of dimethylaminoethyl acrylate was placed in a vertical thin layer distillation device (thin layer distillation column H) and subjected to distillation therein under a reduced pressure of 25 mmHg. At a temperature of 76–79° C., a liquid containing 50 wt. % of dimethylaminoethyl acrylate was distilled. A liquid containing 5 wt. % of dimethylaminoethyl acrylate was obtained through the bottom of the column.

The amount of the dimethylaminoethyl acrylate obtained as described above was 400.2 g and the purity thereof was 99.8 wt. %. The yield of this compound was 93 mol % based on the charged dimethylamino ethanol.

Example I-3

Purification of methanol was carried out by following the procedure of Example I-1 while using a strongly acidic ion-exchange resin (made by the Dow Chemical Company and sold under the trademark designation of "DOWEX-HCR-W-2-H"). The purified alcohol had the following composition.

Composition of Purified Alcohol (Initial Fraction)

Methanol: 48.4 wt. %

Methyl acrylate: 51.3 wt. %

Acetaldehyde: 6 ppm 1,1-Dimethoxyethane: 1800 ppm

Methyl methoxypropionate: 0.1 wt. %

Total nitrogen content: 3 ppm

Even after 200 hours of starting the feed of raw materials, the ion-exchange resin was not colored and the purified alcohol was colorless and transparent.

When the purified alcohol was preserved at 30° C. for 10 days and then analyzed, it had the following composition, showing no change.

Composition of Purified Alcohol (After 10 Days of Preservation)

Methanol: 48.4 wt. %

Methyl acrylate: 51.3 wt. %

Acetaldehyde: 6 ppm 1,1-Dimethoxyethane: 1800 ppm

Methyl methoxypropionate: 0.1 wt. %

Total nitrogen content: 3 ppm

Example II-1

<Step 1: Reaction of Transesterification>

A flask having an inner volume of 3 liters and provided with a stirrer, a thermometer, and a fractional distillation column was charged with 160.5 parts of dimethylamino ethanol, 1704.6 parts of methyl acrylate, 16.0 parts of dibutyl tin oxide as a catalyst, and 8.5 parts of phenothiazine as a polymerization inhibitor. The components in the flask were stirred and heated simultaneously. After they began refluxing, 641.8 parts of dimethylamino ethanol was added thereto so as to prevent the dimethylamino ethanol concentration in the reaction system from exceeding 10 mol %. This addition was made over a period of four hours. The methanol consequently formed was maintained under the conditions of 62–70° C. of column top temperature and 0.5–5.0 of reflux ratio to effect fractional distillation of an azeotropic mixture of methanol and methyl acrylate. The reaction completed in eight hours. When the reaction solution was analyzed, the conversion of dimethylamino ethanol was found to be 95 mol % and the selectivity to dimethylaminoethyl acrylate to be 98 mol %.

<Step 2: Distillation>

The distillate obtained at the step 1 was distilled by the use of a fractional distillation device under normal pressure. Under the conditions of 1.5 of reflux ratio and 62° C. of column top temperature, an azeotropic fraction of methanol and methyl acrylate was extracted through the top of the column and methyl acrylate was extracted through the bottom of the column. The methanol/methyl acrylate fraction obtained through the column top was analyzed. The result was as shown below.

Methanol: 48.5 wt. %

Methyl acrylate: 51.3 wt. %

Acetaldehyde: 890 ppm 1,1-Dimethoxyethane: 70 ppm

Methyl methoxypropionate: 0.1 wt. %

Total nitrogen content: 93 ppm

<Step 3: Purification with Ion-exchange Resin>

The methanol/methyl acrylate distillate obtained at the step 2 was passed at normal temperature under normal pressure to a column packed with 200 ml of a weakly acidic ion-exchange resin (made by Mitsubishi Chemical Co., Ltd. and sold under the trademark designation of "Diaion WK-40"). The purified methanol/methyl acrylate distillate was analyzed. The result is shown in Table 1 (initial stage of storage).

Even after 200 hours of starting the feed of raw materials, the ion-exchange resin was not colored and the purified methanol/methyl acrylate distillate was colorless and transparent.

<Test of 30° C. Storage>

When the purified methanol/methyl acrylate distillate was preserved at 30° C. for 10 days and then analyzed, the result was as shown in Table 1.

Comparative Example II-1

The methanol/methyl acrylate distillate from the step 2 of Example II-1 was subjected, omitting the step 3, to the test of 30° C. storage and then analyzed. The result was as shown in Table 1.

TABLE 1

|  | Example II-1 | | Comparative Example II-1 | |
| --- | --- | --- | --- | --- |
|  | Initial stage of storage | After elapse of 10 days | Initial stage of storage | After elapse of 10 days |
| Methanol (wt %) | 11 | 11 | 48.3 | 48.0 |
| Methyl acrylate (wt %) | 89 | 89 | 51.3 | 50.1 |
| Acetaldehyde (ppm) | 890 | 890 | 890 | 890 |

TABLE 1-continued

|  | Example II-1 | | Comparative Example II-1 | |
| --- | --- | --- | --- | --- |
|  | Initial stage of storage | After elapse of 10 days | Initial stage of storage | After elapse of 10 days |
| 1,1-Dimethoxyethane ppm) | 70 | 70 | 70 | 70 |
| Methyl methoxypropionate (wt %) | 0.1 | 0.1 | 0.1 | 1.8 |
| Total nitrogen content (ppm) | 18 | 18 | 93 | 93 |

It is noted from the result given above that when the total nitrogen content was 93 ppm, the preservation lowered the concentrations of methanol and methyl acrylate and by-produced methyl methoxypropionate as an impurity.

Example II-2

Production of methanol/methyl acrylate was carried out by following the procedure of Example II-1 while using a strongly acidic ion-exchange resin (made by the Dow Chemical Company and sold under the trademark designation of "DOW-HCR-W2-H") as an ion-exchange resin at the step 3. The purified methanol/methyl acrylate distillate was subjected to the test of 30° C. storage and then analyzed. The result was as shown in Table 2.

Even after 200 hours of starting the feed of raw materials, the ion-exchange resin was not colored and the purified methanol/methyl acrylate distillate was colorless and transparent.

Example II-3

In a separation funnel, 1 liter in volume, 300 g of the methanol/methyl acrylate distillate obtained at the step 2 of Example II-1 was placed and 300 g of water was added thereto and mixed therewith and the resultant mixture was left standing at rest and separate into two layers. The oil phase obtained after the separation into the two layers was subjected to the test of 30° C. storage in the same manner as in Example II-1. The sample after the test of 30° C. storage was analyzed. The result was as shown in Table 2.

Example II-4

In a separation funnel, 1 liter in volume, 300 g of the methanol/methyl acrylate distillate obtained at the step 2 of Example II-1 was placed and 300 g of an aqueous 1% acrylic acid solution was added thereto and mixed therewith and the resultant mixture was left standing at rest and separate into two layers. The oil phase obtained after the separation into the two layers was subjected to the test of 30° C. storage in the same manner as in Example II-1. The sample after the test of 30° C. storage was analyzed. The result was as shown in Table 2.

TABLE 2

|  | Example II-2 | | Example II-3 | | Example II-4 | |
| --- | --- | --- | --- | --- | --- | --- |
|  | Initial stage of storage | After elapse of 10 days | Initial stage of storage | After elapse of 10 days | Initial stage of storage | After elapse of 10 days |
| Methanol (wt %) | 11 | 11 | 48.5 | 48.5 | 48.4 | 48.4 |
| Methyl acrylate (wt %) | 89 | 89 | 51.3 | 51.3 | 51.3 | 51.3 |

TABLE 2-continued

|  | Example II-2 | | Example II-3 | | Example II-4 | |
| --- | --- | --- | --- | --- | --- | --- |
|  | Initial stage of storage | After elapse of 10 days | Initial stage of storage | After elapse of 10 days | Initial stage of storage | After elapse of 10 days |
| Acetaldehyde (ppm) | 6 | 6 | 890 | 890 | 6 | 6 |
| 1,1-Dimethoxy-ethane (ppm) | 1800 | 1800 | 70 | 70 | 1800 | 1800 |
| Methyl methoxy-propionate (wt %) | 0.1 | 0.1 | 0.1 | 0.1 | 0.1 | 0.1 |
| Total nitrogen content (ppm) | 4 | 4 | 3 | 3 | 3 | 3 |

Example II-5
<Step 1: Reaction of Transesterification>

A flask having an inner volume of 5 liters and provided with a stirrer, a thermometer, and a fractional distillation column was charged with 160.5 parts of dimethylamino ethanol, 2539.5 parts of n-butyl acrylate, 16.0 parts of dibutyl tin oxide as a catalyst, and 8.5 parts of phenothiazine as a polymerization inhibitor. The components in the flask were stirred and heated simultaneously under a reduced pressure of 300 Torrs. After they began refluxing, 641.8 parts of dimethylamino ethanol was added thereto so as to prevent the dimethylamino ethanol concentration in the reaction system from exceeding 10 mol %. This addition was made over a period of four hours. The n-butanol consequently formed was maintained under the conditions of 62–70° C. of column top temperature and 0.5–5.0 of reflux ratio to effect fractional distillation of an azeotropic mixture of n-butanol and n-butyl acrylate. The reaction completed in seven hours. When the reaction solution was analyzed, the conversion of dimethyl-amino ethanol was found to be 95 mol % and the selectivity to dimethylamino acrylate to be 98 mol %.

<Step 2: Distillation>

The distillate obtained at the step 1 was distilled by the use of a fractional distillation device under normal pressure. Under the conditions of 300 mmHg of column top pressure and 96° C. of column top temperature, an azeotropic fraction of n-butanol/n-butyl acrylate was extracted through the top of the column and n-butyl acrylate was extracted through the bottom of the column. The n-butanol/n-butyl acrylate distillate obtained through the column top was analyzed. The result was as shown below.

n-Butanol: 92.1 wt. % n-Butyl acrylate: 7.8 wt. %

Acetaldehyde: 890 ppm 1,1-Di-n-butoxyethane: 10 ppm

Butyl butoxypropionate: 200 ppm

Total nitrogen content: 93 ppm

<Step 3: Purification with Ion-exchange Resin>

The n-butanol/n-butyl acrylate distillate obtained at the step 2 was passed at normal temperature under normal pressure to a column packed with 200 ml of a weakly acidic ion-exchange resin (made by Mitsubishi Chemical Co., Ltd. and sold under the trademark designation of "Diaion WK-40"). The purified n-butanol/n-butyl acrylate distillate was analyzed. The result is shown in Table 3 (initial stage of storage).

Even after 200 hours of starting the feed of raw materials, the ion-exchange resin was not colored and the purified n-butanol n-butyl acrylate distillate was colorless and transparent.

<Test of 30° C. Storage>

When the purified n-butanol/n-butyl acrylate distillate was preserved at 30° C. for 10 days and then analyzed, the result was as shown in Table 3.

TABLE 3

|  | Example II-5 | |
| --- | --- | --- |
|  | Initial stage of storage | After elapse of 10 days |
| n-Butanol (wt %) | 92.1 | 92.1 |
| n-Butyl acrylate (wt %) | 7.8 | 7.8 |
| Acetaldehyde (ppm) | 140 | 140 |
| 1,1-Dimethoxybutane (ppm) | 10 | 10 |
| Butyl buthoxypropionate (wt %) | 200 | 200 |
| Total nitrogen content (ppm) | 3 | 3 |

Example II-6
<Step 1: Reaction of Transesterification>

A flask having an inner volume of 3 liters and provided with a stirrer, a thermometer, and a fractional distillation column was charged with 160.5 parts of dimethylamino ethanol, 1983.2 parts of methyl methacrylate, 16.0 parts of dibutyl tin oxide as a catalyst, and 8.5 parts of phenothiazine as a polymerization inhibitor. The components in the flask were stirred and heated simultaneously. After they began refluxing, 641.8 parts of dimethylamino ethanol was added thereto so as to prevent the dimethylamino ethanol concentration in the reaction system from exceeding 10 mol %. This addition was made over a period of four hours. The methanol consequently formed was maintained under the conditions of 62–70° C. of column top temperature and 0.5–5.0 of reflux ratio to effect fractional distillation of an azeotropic mixture of methanol/methyl methacrylate. The reaction completed in eight hours. When the reaction solution was analyzed, the conversion of dimethylamino ethanol was found to be 95 mol % and the selectivity to dimethylamino methacrylate to be 98 mol %.

<Step 2: Distillation>

The distillate obtained at the step 1 was distilled by the use of a fractional distillation device under normal pressure. Under the condition of 64.2° C. of column top temperature, an azeotropic fraction of methanol/methyl methacrylate was extracted through the top of the column and methyl acrylate was extracted through the bottom of the column. The methanol/methyl methacrylate distillate obtained through the top of the column was analyzed. The result was as shown below.

Methanol: 81.6 wt. %

Methyl methacrylate: 18.3 wt. %

Acetaldehyde: 730 ppm 1,1-Dimethoxyethane: 70 ppm

Methyl methoxyisobutanoate: 290 ppm

Total nitrogen content: 84 ppm

<Step 3: Purification with Ion-exchange Resin>

The methanol/methyl methacrylate distillate obtained at the step 2 was passed at normal temperature under normal pressure to a column packed with 200 ml of a weakly acidic ion-exchange resin (made by Mitsubishi Chemical Co., Ltd. and sold under the trademark designation of "Diaion WK-40"). The purified methanol/methyl acrylate distillate was analyzed. The result is shown in Table 4 (initial stage of storage).

Even after 200 hours of starting the feed of raw materials, the ion-exchange resin was not colored and the purified alcohol was colorless and transparent.

<Test of 30° C. Storage>

When the purified methanol/methyl methacrylate distillate was preserved at 30° C. for 10 days and then analyzed, the result was as shown in Table 4.

TABLE 4

|  | Example II-6 | |
| --- | --- | --- |
|  | Initial stage of storage | After elapse of 10 days |
| Methanol (wt %) | 81.6 | 81.6 |
| Methyl acrylate (wt %) | 18.3 | 18.3 |
| Acetaldehyde (ppm) | 560 | 560 |
| 1,1-Dimethoxyethane (ppm) | 80 | 80 |
| Methyl methoxypropionate (wt %) | 290 | 290 |
| Total nitrogen content (ppm) | 3 | 3 |

Referential Example

In a flask having an inner volume of 3 liters and provided with a stirrer, a cooling device, a dropping device, and a fractional distillation column, 100 parts of a strongly acidic ion-exchange resin (made by the Dow Chemical Company and sold under the trademark designation of "DOW-HOR-W2-H") was placed as a catalyst and 500 parts of the purified methanol/methyl acrylate distillate obtained at the step 3 of Example II-1, 242.6 parts of methanol, 1091 parts of acrylic acid, and 0.33 part of hydroquinone monomethyl ether as a polymerization inhibitor were added and solved and they were subjected to a treatment of esterification under normal pressure at 70° C. A methanol/methyl acrylate azeotropic fraction was continuously extracted through the top of the column and a mixed liquid equal in amount was continuously introduced into the flask. Even after 200 hours of starting the distillation, the catalyst showed no sign of loss of activity.

When the procedure mentioned above was repeated by using the methanol/methyl acrylate distillate obtained at the step 2 of Example II-1 in a state not purified with an ion-exchange resin in the place of the purified methanol/methyl acrylate distillate obtained at the step 3 of Example II-1, the distillation temperature began to rise and the catalyst showed a discernible decline of activity after 100 hours of starting the distillation.

Example III-1

Production of dimethylaminoethyl acrylate was performed by following the procedure of the process diagram illustrated in FIG. 3.

Step 1:

A flask (reaction vessel A) having an inner volume of 3 liters and provided with a stirrer, a thermometer, and a fractional distillation column (alcohol distillation column B) was charged with 160.5 parts of dimethylamino ethanol, 1704.6 parts of methyl acrylate, 16.0 parts of dibutyl tin oxide as a catalyst, and 8.5 parts of phenothiazine as a polymerization inhibitor. The components in the flask were stirred and heated simultaneously. After they began refluxing, 641.8 parts of dimethylamino ethanol was added thereto so as to prevent the dimethylamino ethanol concentration in the reaction system from exceeding 10 mol %. This addition was made over a period of four hours. The methanol by-produced in the reaction under the conditions of 62–70° C. of column top temperature and 0.5–5.0 of reflux ratio was distilled in the form of an azeotropic mixture with methyl acrylate. The reaction completed in eight hours. When the reaction solution was analyzed, the conversion of dimethylamino ethanol was found to be 95 mol % and the selectivity to dimethylaminoethyl acrylate to be 98 mol %.

Step 2:

The reaction solution of the step 1 was introduced into a distillation apparatus, Oldershaw column type fractional distillation device (distillation column J) and subjected to distillation therein under the conditions of 85 mmHg of column top pressure, 70° C. of column bottom temperature, and 30 minutes of column interior retention time, with the result that methyl acrylate was recovered through the top of the column.

Step 3:

The bottoms of the step 2 was placed in a vertical thin layer distillation column (catalyst recovery column K) and subjected to distillation therein under the conditions of 15 mmHg of pressure, 110° C. of column interior temperature, and 30 seconds of column interior retention time to obtain a distillate having a dimethylaminoethyl acrylate content of 73 wt. % through the top of the column and a liquid containing dibutyl tin oxide and phenothiazine (recovered catalyst liquid) through the bottom of the column.

The ratio of increase of the Michael adduct at the step 2 and the step 3 mentioned above was 0.48%. The recovered catalyst liquid was found to contain no discernible viscous substance.

Step 4:

The distillate having a dimethylaminoethyl acrylate content of 73 wt. % and emanating from the step 3 was introduced into a fractional distillation column (light boiling separation column F) and subjected to distillation therein under the condition of 40 mmHg of column top pressure. Under the conditions of 50° C. of column top temperature and 5–20 of reflux ratio, methyl acrylate and dimethylamino ethanol were extracted through the top of the column and a liquid having a dimethylaminoethyl acrylate content of 93 wt. % was obtained through the bottom of the column.

Step 5:

The bottoms having a dimethylaminoethyl acrylate content of 93 wt. % and emanating from the step 4 was introduced into a fractional distillation column (rectifying column G) and subjected to distillation therein under the reduction condition of 25 mmHg of column top pressure. Under the condition of 76–79° C. of column top temperature, dimethylaminoethyl acrylate was extracted through the top of the column and a liquid containing 70 wt. % of dimethylaminoethyl acrylate and 30 wt. % of a high boiling impurity was obtained through the bottom of the column.

Step 6:

The bottoms having a dimethylaminoethyl acrylate content of 70 wt. % and emanating from the step 5 were introduced into a vertical thin layer distillation column (thin layer distillation column H) and subjected to distillation therein under a reduced pressure of 25 mmHg. At a temperature of 76–79° C., a distillate having a dimethylaminoethyl acrylate content of 50 wt. % was extracted through the top of the column and a liquid containing 5 wt. % of diethylaminoethyl acrylate and 95 wt. % of a high boiling impurity was obtained through the bottom of the column.

The amount of the dimethylaminoethyl acrylate thus obtained was 418.6 parts and the purity thereof was 99.8%. The yield was 94.5 mol % based on the charged dimethylamino ethanol.

Example III-2

The procedure of Example III-1 was repeated, excepting that the step 2 and the step 3 thereof were altered as follows.
Step 2:
The reaction solution obtained at the step 1 was introduced into a fractional distillation column (distillation column J) and subjected to distillation under the reduction conditions of 100 mmHg of column top pressure, 120° C. of column bottom temperature, and 30 minutes of column interior retention time, with the result that methyl acrylate was recovered through the top of the column.
Step 3:
The bottoms obtained at the step 2 was placed in a vertical thin layer distillation column (catalyst recovery column K) and subjected to distillation therein under the conditions of 40 mmHg of pressure, 110° C. of column interior temperature, and 30 seconds of column interior retention time, with the result that a distillate having a dimethylaminoethyl acrylate content of 73 wt. % was obtained through the top of the column and a liquid containing dibutyl tin oxide and phenothiazine (recovered catalyst liquid) was obtained through the bottom of the column.

The ratio of increase of the Michael adduct at the step 2 and the step 3 mentioned above was 0.96%. The recovered catalyst liquid was found to contain no discernible viscous substance.

The amount of the dimethylaminoethyl acrylate obtained by the procedure mentioned above was 408.7 parts and the purity thereof was 99.8%. The yield was 92.6 mol % based on the charged dimethylamino ethanol.

Example III-3

In the procedure of Example III-1, the separation of the catalyst was effected by using one distillation device in place of the two distillation devices at the step 2 and the step 3.

In a flask having an inner volume of 3 liters and provided with a stirrer, a thermometer, an air inlet pipe, and a distillation column, the reaction solution obtained at the step 1 was placed and subjected to distillation therein under the conditions of 250–100 mmHg of column top pressure and 75–95° C. of flask interior temperature to recover methyl acrylate through the top of the column. The duration of the reaction was four hours. Then, under the conditions of 100–10 mmHg of column top pressure and 80–110° C. of flask interior temperature, a liquid having a dimethylaminoethyl acrylate was obtained through the top of the column. The duration of the operation was four hours.

The ratio of increase of the Michael adduct in the procedure mentioned above was 2.2%.

From this point onward (at and after the step 4), the procedure of Example III-1 was followed. The amount of dimethylaminoethyl acrylate thus obtained was 394.8 parts and the purity thereof was 99.8 wt. %. The yield was 92.0 mol % based on dimethylamino ethanol. The recovered catalyst was found to contain a viscous substance in a small amount.

While the embodiments or examples of the present invention, as herein disclosed, constitute a preferred form, it is to be understood that other form might be adopted.

The entire disclosure of Japanese Patent Application No. 9-268462 filed on Oct. 1, 1997, Japanese Patent Application No. 9-359412 filed on Dec. 26, 1998, and Japanese Patent Application No. 9-359413 filed on Dec. 26, 1998 including specification, claims, drawing and summary are incorporated herein by reference in its entirety.

What is claimed is:

1. A method for producing an alkylamino(meth)acrylate represented by the formula (3):

$$H_2C=C(R^1)-C(=O)-O-R^5-N(R^3)(R^4) \quad (3)$$

the symbols are the same as below, which comprises the steps of
 (i) carrying out, in the presence of a catalyst, the reaction of transesterification of an alkyl(meth)acrylate represented by the formula (1):

$$H_2C=C(R^1)-COOR^2 \quad (1)$$

wherein $R^1$ is a hydrogen atom or methyl group, $R^2$ an alkyl group having 1 to 4 carbon atoms, with an alkylamino alcohol represented by the formula (2):

$$R^3(R^4)N-R^5-OH \quad (2)$$

wherein $R^3$ is a hydrogen atom or alkyl group having 1 to 8 carbon atoms, $R^4$ an alkyl group having 1 to 8 carbon atoms, and $R^5$ an alkylene group having 1 to 4 carbon atoms,
 (ii) causing an alkyl alcohol by-produced during the transesterification to be distilled in the form of an azeotropic mixture with the alkyl(meth)acrylate, and
 (iii) purifying the resultant azeotropic mixture with a weekly acidic ion-exchange resin thereby recovering the alkyl alcohol.

2. A method according to claim 1, further comprising distilling the azeotropic mixture before the purification step.

3. A method according to claim 1, wherein the total nitrogen content in the recovered alcohol in step (iii) is not more than 0.002% by weight, based on the weight of the recovered alcohol.

4. A method according to claim 1, wherein the purification with an ion-exchange resin in step (iii) is carried out in the presence of water.

5. A method according to claim 4, wherein the amount of water during the purification is in the range of 0.05–100% by weight, based on the amount of the distillate containing alkyl(meth)acrylate and alkyl alcohol to be added.

6. A method for handling the recovered alkyl alcohol according to claim 3 at a temperature in the range of 0–50° C.

7. A method according to claim 1, further comprises distilling the reaction solution from the transesterification in step (i) to separate the catalyst.

8. A method according to claim 1, wherein the distillation on the reaction solution resulting from the reaction of transesterification for the purpose of separating the catalyst is carried out under a condition such that the ratio of increase of the Michael adduct is not more than 2%.

9. A method according to claim 7, wherein the step for separating the catalyst in distilling the reaction solution from the transesterification in step (i) comprising supplying the reaction solution to a first distillation column wherein the reaction solution is distilled thereby removing the distillate containing the alkyl(meth) acrylate through the top thereof and supplying the removed distillate to the transesterification reaction vessel in step (i), supplying the bottom emanating from the first distillation column to a second distillation column wherein a distillate containing the alkylamino(meth)acrylate is removed through the top thereof and the catalyst is separated through the bottom thereof, supplying the distillate emanating from the second distillation column to a light boiling separation column thereby expelling a light boiling substance through the top thereof and supplying the light boiling substance to the transesterification reaction vessel in step (i), and supplying the bottom emanating from the light boiling separation column to a rectifying column thereby obtaining the alkylamino(meth)acrylate aimed at through the top thereof.

10. A method according to claim 9, wherein the distillation in the first distillation column is carried out under the conditions of 60–120° C. of column bottom temperature and two seconds–two hours of retention time and the distillation in the second distillation column is carried out under the conditions of 60–120° C. of column bottom temperature and two seconds–one hour of retention time.

11. A method according to claim 1, wherein the ion-exchange resin is a weakly acidic ion-exchange resin containing a carboxyl group as an ion-exchange group.

12. A method according to claim 4, wherein the amount of water during purification is in the range of 0.1 to 50% by weight, based on the amount of the distillate containing an alkyl(meth)acrylate and alkyl alcohol to be added.

13. A method according to claim 12, wherein the amount of water during purification is in the range of 0.2 to 20% by weight, based on the amount of the distillate containing an alkyl(meth)acrylate and alkyl alcohol to be added.

14. A method according to claim 6, wherein the temperature is in the range of 5 to 40° C.

15. A method according to claim 1, wherein the alkylamino(meth)acrylate is at least one member selected from the group consisting of dimethylamino ethyl(meth) acrylate, diethylamino ethyl(meth)acrylate, dimethylamino propyl(meth)acrylate, dimethylamino butyl(meth)acrylate, and dibutylamino ethyl(meth)acrylate.

16. A method according to claim 3, wherein the total nitrogen content is not more than 0.001% by weight, based on the weight of the recovered alcohol.

* * * * *